United States Patent [19]
Evans et al.

[11] Patent Number: 5,110,966
[45] Date of Patent: May 5, 1992

[54] NEW ORGANOBORON REAGENTS FOR THE PREPARATION OF UNSUBSTITUTED PROPARGYLIC ALCOHOLS

[75] Inventors: Jonathan C. Evans; Christian T. Goralski, both of Midland, Mich.

[73] Assignee: Merrell Dow Pharmaceuticals Inc., Cincinnati, Ohio

[21] Appl. No.: 717,970

[22] Filed: Jun. 20, 1991

[51] Int. Cl.$^5$ .............................. C07F 5/02
[52] U.S. Cl. ................................. 556/403
[58] Field of Search ...................... 556/403

[56] References Cited

U.S. PATENT DOCUMENTS 4,537,773  8/1985  Sheravi ................ 556/403 X
4,644,075  2/1987  Masamune ............ 556/403

OTHER PUBLICATIONS

Brown, H.C. and Sinclair, J.A.: Organoboranes. XVIII Reaction of Lithium Alkynes with Methyl Dialkylborinates: The Synthesis of B-1-Alkynyldialkylboranes. Journal of Organometallic Chemistry, 131, 163–169 (1977).

Brown, H.C., et al.: Organoboranes. 38. A Facile and Highly Efficient Addition of B-1-Alkynyl-9-borabicyclo[3.3.1]nonanes to Aldehydes and Ketones: An Exceptionally Chemoselective Synthesis of Propargylic Alcohols Primary Examiner—Paul F. Shaver
Attorney, Agent, or Firm—Louis J. Wille

[57] ABSTRACT

The novel organoboron reagent of the present invention is useful in the preparation of unsubstituted propargylic alcohols. This compound reacts with aldehydes and ketones cleanly to afford propargylic alcohols in excellent yields. Unsubstituted propargylic alcohols are important synthetic intermediates in the synthesis of a number of natural products. In addition, the novel organoboron reagent of the present invention also demonstrates diastereomeric selectivity when reacted with enatiomerically pure aldehydes.

2 Claims, No Drawings

NEW ORGANOBORON REAGENTS FOR THE PREPARATION OF UNSUBSTITUTED PROPARGYLIC ALCOHOLS

BACKGROUND OF THE INVENTION

The present invention relates to novel organoboron reagents which are useful in the preparation of unsubstituted propargylic alcohols.

Unsubstituted propargylic alcohols are important intermediates in the synthesis of a number of natural products, including the prostaglandins [Ann. N.Y. Acad. Sci. 180 38 1971, Prostaglandins 10 503 1975 and Ann. N.Y. Acad. Sci. 180 64 1971], steroids [J.Am. Chem. Soc. 99 8341 1977], carotenoids [J. Org. Chem. 41 3497 1976]and leukotrienes [J. Am. Chem. Soc. 106 3548 1984]. Unsubstituted propargylic alcohols are defined as those propargylic alcohols bearing a terminal hydrogen on the acetylenic functionality.

Propargylic alcohols have been prepared by a number of methods. The addition of alkynylmetals to aldehydes is one such method of preparing propargylic alcohols [Hebd. Seances Aced. Sci. 261 1992 1965, Bull. Soc. Chim. Fr. 205 1968, Hebd. Seances Aced. Sci., Seances Ser. C 289 1966, "Chemistry of Alkylenes"; Marcel Dekker; New York, 1969, Bull. Soc. Pharm. Bordeaux 101, 3 1962, J. Org. Chem. 38 3588 1973, Chem. Ber. 92 1270 1959, Chem. Ber 92 541 1959, J. Am. Chem. Soc. 87 5632 1965, Bull. Soc. Chim. Fr. 1447 1957. These alkynylmetal reagents are highly basic and can cause unwanted base-induced eliminations. They are also highly nucleophilic and react with a variety of functional groups, thus restricting their versatility in the synthesis of complex organic molecules. In addition, except for the alkynyllithium, the preparation of alkynylmetals is often inconvenient due to the physical properties of the metals (i.e., flamability, reactivity, etc.). Also, in many cases, these metal complexes contain a number of alkyne ligands, but only successfully transfer one alkyne ligand.

Another method of preparing propargylic alcohols is the addition of B-1-alkynyl-9-borabicyclo[3.3.1]nonane reagents to aldehydes and ketones [J. Org. Chem. 50 1577 1985, J. Organometal. Chem. 131 163 1977]. These reagents are very mild and show no reactivity toward a variety of functional groups such as esters, nitriles, acetals, ketals, acid chlorides, alkyl halides, and amides. In contrast to the alkynylmetal reagents, the B-1-alkynyl-9-borabicyclo[3.3.1]nonane reagents react cleanly with aldehydes and ketones to afford the corresponding propargylic alcohols. The B-1-alkynyl-9-borabicyclo[3.3.1]nonane reagents can also preferentially react with aldehydes in the presence of ketones and also demonstrate stereoselectivity [J. Organometal. Chem. 131 163 1977]. This reagent would have been useful in the preparation of a class of unsubstituted propargylic alcohols which are important synthetic intermediates in the synthesis of a number of natural products. Attempts to prepare B-ethynyl-9 -borabicyclo[3.3.1]nonane, however, were unsuccessful [J. Organometal. Chem. 131 163 1977].

The novel organoboron reagents of the present invention are useful in the preparation of propargylic alcohols. These compounds react with aldehydes and ketones cleanly to afford propargylic alcohols in excellent yields and are useful in the preparation of a class of unsubstituted propargylic alcohols which are important synthetic intermediates in the synthesis of a number of natural products. Unlike the alkynylmetal reagents, the novel organoboron reagents of the present invention are convenient to prepare and can be stored as solutions at $-40°$ C. to $-10°$ C. for up to one week. The reagents can be isolated as 1:1 tetrahydrofuran complexes. These complexes are stable crystalline solids which have been stored at room temperature under an argon atmosphere for up to 6 months. In addition, the novel organoboron reagents of the present invention also demonstrate diastereomeric selectivity when reacted with enatiomerically pure aldehydes.

SUMMARY OF THE INVENTION

The present invention provides novel compounds of the formula (I)

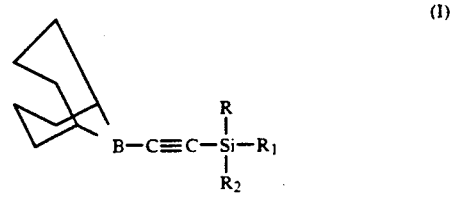

wherein R, $R_1$ and $R_2$ are each independently selected from a group consisting of $C_1-C_6$ alkyl and phenyl. It is preferred that R, $R_1$ and $R_2$ are each represented by $CH_3$.

The present invention further provides a method of using the compounds of formula (I) comprising the steps of (a) reacting a compound of the formula (I) with an appropriate aldehyde or ketone to give a 1-trisubstitutedsilyl-1-alkyn-3 -ol and (b) reacting said 1-trisubstitutedsilyl-1-alkyn-3-ol with a suitable fluoride source. It is preferred that R, $R_1$ and $R_2$ are each represented by $CH_3$.

The present invention further provides a process for preparing unsubstituted propargylic alcohols comprising the steps of (a) reacting a compound of the formula (I) with an appropriate aldehyde or ketone to give a 1-trisubstituted-silyl-1-alkyn-3-ol and (b) reacting said 1-trisubstituted-silyl-1-alkyn-3-ol with a suitable fluoride source. It is preferred that R, $R_1$ and $R_2$ are each represented by $CH_3$.

DETAILED DESCRIPTION OF THE INVENTION

As used herein, the term "$C_1-C_6$ alkyl" refers to a saturated hydrocarbyl radical of from 1 to 6 carbon atoms of straight, branched or cyclic configuration. Specifically included within the scope of the term are $-CH_3$, $-CH_2CH_3$, $-CH_2CH_2CH_3$, $-CH(CH_3)_2$, $-CH_2(CH_2)_2CH_3$, $-C(CH_3)_3$, $-CH_2(CH_2)_3-CH_2(CH_2)_4CH_3$, cyclohexyl and the like.

The term "$C_1-C_{12}$ alkyl" refers to a saturated hydrocarbyl radical of from 1 to 12 carbon atoms of straight, branched or cyclic configuration. Specifically included within the scope of the term are $-CH_3$, $-CHhd 2CH_3$, $-CH_2CH_2CH_3$, $-CH(CH_3)_2$, $-CH_2(CH_2)_2CH_3$, $-C(CH_3)_3$, $-CH_2(CH_2)_3CH_3$, $-CH_2(CH_2)_4CH_3$, $-CH_2(CH_2)_5CH_3$, $-CH_2(CH_2)_6CH_3$, $-CH_2(CH_2)_7CH_3$, $-CH_2(CH_2)_8CH_3$, cyclohexyl and the like.

The term "$C_5-C_7$ cycloalkyl" refers to a cycloalkyl group containing 5-7 carbon atoms including cyclohexyl, cyclopentyl and cycloheptyl.

The term "halogen" refers to a chlorine, bromine, iodine or fluorine atom.

The term "$C_1$-$C_6$ alkoxy" refers to a alkoxy group containing 1-6 carbons atoms of straight or branched configuration including methoxy, ethoxy, propoxy and the like.

The compounds of formula (I) can be prepared by utilizing procedures and techniques well known and appreciated by one of ordinary skill in the art. A general synthetic procedure for preparing these compounds is set forth in Scheme A.

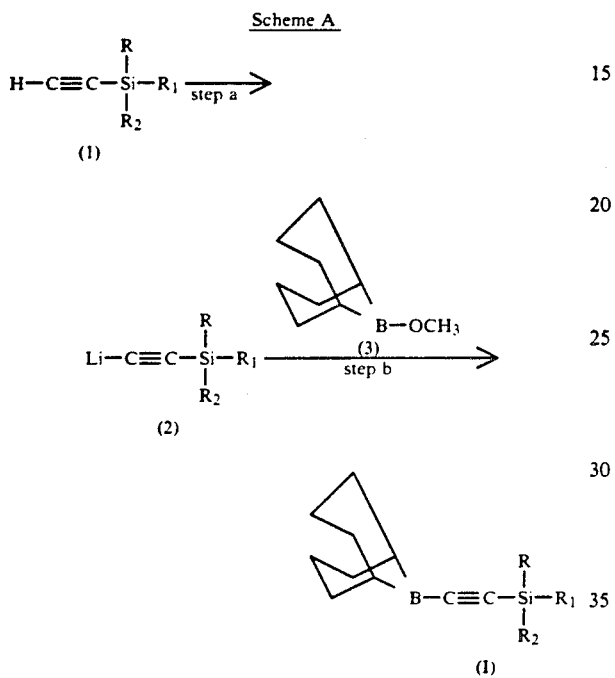

Scheme A

Scheme A provides a synthetic procedure for preparing the compounds of formula (I).

In step a, the appropriate trisubstituted-silylacetylene of structure (1) is converted to the corresponding lithium trisubstitutedsilylacetylene of structure (2).

For example, the appropriate trisubstituted-silylacetylene of structure (1) is contacted with a molar equivalent of a suitable alkyl lithium reagent such as n-butyllithium, sec-butyllithium, t-butyllithium, lithium hexamethyldisilazane and the like with n-butyllithium being preferred. The reactants are typically contacted in a suitable anhydrous organic solvent such as tetrahydrofuran, hexane, pentane, diethyl ether, t-butyl methyl ether and the like with tetrahydrofuran being preferred. The reactants are typically stirred together under an inert atmosphere for a period of time ranging from 5 minutes to 24 hours and at a temperature range of from −78° C. to room temperature. A temperature range of −78° C. to −40° C. and a reaction time of 15 minutes to 1 hour are preferred. The resulting lithium trisubstitutedsilylacetylene of structure (2) may be used in situ in step b.

An appropriate trisubstitutedsilylacetylene of structure (1) is one wherein R, $R_1$ and $R_2$ are each independently selected from a group consisting of $C_1$-$C_6$ alkyl and phenyl. It is preferred that R, $R_1$ and $R_2$ are each $CH_3$.

In step b, the appropriate lithium trisubstituted-silylacetylene (2) is coupled with B-methoxy-9-borabicyclo[3.3.1]nonane (3) to give the corresponding B-(2-(trisubstitutedsilyl)ethynyl)-9-borabicyclo[3.3.1]nonane of formula (I).

For example, the appropriate lithium trisubstituted-silylacetylene (2) is contacted with an equimolar amount of B-methoxy-9-borabicyclo[3.3.1]nonane (3) in a suitable anhydrous inert organic solvent such as tetrahydrofuran, hexane, t-butyl methyl ether, diethyl ether, pentane and the like with tetrahydrofuran being preferred. The reactants are typically stirred together under an inert atmosphere for a period of time ranging from 5 minutes to 48 hours at a temperature range of from −78° C. to room temperature. A temperature range of −78° C. to −40° C. and a reaction time of 1.5 hours to 5 hours are preferred. The intermediate "ate" complex thus formed is contacted with a molar excess of a suitable lewis acid such as boron trifluoride etherate, boron trichloride and the like with boron trifluoride etherate being preferred. The reactants are typically stirred together under an inert atmosphere for a period of time ranging from 5 minutes to 24 hours and at a temperature range of from −78° C. to room temperature. A temperature range of −78° C. to −40°0 C. and a reaction time of 15 minutes to 1 hour are preferred. The B-(2-(trisubstitutedsilyl)ethynyl)-9 -borabicyclo[3.3.1]nonane of formula (I) is isolated as a tetrahydrofuran complex by evaporation of the volatiles. It may be purified by crystallization from a suitable inert organic solvent such as pentane, hexane and the like. Starting materials for use in Scheme A are readily available to one of ordinary skill in the art.

The following example presents a typical synthesis of the compounds of formula (I) as described in Scheme A. This example is understood to be illustrative only and is not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C" refers to degrees Celsius; "mm Hg" refers to millimeters of mercury; "μL" refers to microliters; "μg" refers to micrograms; and "μM" refers to micromolar.

EXAMPLE 1

B-(2-(Trimethylsilyl)ethynyl)-9-borabicyclo[3.3.1-]nonane.tetrahydrofuran complex Dissolve trimethylsilylacetylene (3.5 mL, 25 mmol) in tetrahydrofuran (40 mL) and cool to −78° C. Add, by dropwise addition, n-butyllithium (10.4 mL of a 2.5N solution, 26mmol) and stir at −78° C. for 15 minutes. Add B-methoxy-9-borabicyclo[3.3.1]nonane (25 mL of a 1M solution, stir at −78° C. for 1.5 hours. Add boron trifluoride etherate (4.0 mL, 33 mmol), stir at −78° C. for 15 minutes and allow to warm to room temperature. Evaporate the volatiles in vacuo the add pentane (25 mL). Stir the suspension for a few minutes, allow to settle and decant the supernatant liquid carefully via a double-ended needle to a second flask. Wash the remaining solid with pentane (2×10 mL) and combine the extracts. Cool the pentane extracts to −78° C. to precipitate the product. Remove the mother liquor and dry the crystals (vacuum) to give the title compound as a white crytalline material (6.52 g, 90%, extremely hygroscopic).

$11_B$ NMR (THF−$d_8$) δ−9.06 (s); $^{29}Si$ NMR (THF−$d_8$) δ−22.67 (s); $^{13}C$ NMR (THF-$d_8$) 103.5, 31.93, 26.19, 0.787 ppm; $^1H$ NMR (THF-$d_8$) δ0.601 (s, 9H), 1.29 (br, 2H), 1.92 (m, 2H), 2.11 (m, 4H), 2.29 (m, 10H), 4.14 (m, 4H); IR (CCl$_4$) 2187 cm$^{-1}$.

The following compounds can be prepared in a similar manner to that described in Example -1:

B-(2-(t-butyldimethylsilyl)ethynyl)-9-borabicyclo[3.3.1]nonane;

B-(2-(diphenylmethylsilyl)ethynyl)-9-borabicyclo[3.3.1]nonane;

B-(2-(triphenylsilyl)ethynyl)-9-borabicyclo[3.3.1]nonane;

B-(2-(dimethylphenylsilyl)ethynyl)-9-borabicyclo[3.3.1]nonane;

B-(2-(dimethylhexylsilyl)ethynyl-9-borabicyclo[3.3.1]nonane.

The compounds of formula (I) can be used to prepare unsubstituted propargylic alcohols. Unsubstituted propargylic alcohols are useful in the synthesis of a number of natural products, including the prostaglandins [*Ann. N.Y. Acad. Sci.* 180 38 1971, *Prostaglandins* 10 503 1975 and *Ann. N.Y. Acad. Sci.* 180 64 1971, steroids [*J. Am. Chem. Soc.* 99 8341 1977], carotenoids [*J. Org. Chem.* 41 3497 1976] and leukotrienes [*J. Am. Chem. Soc.* 106 3548 1984]. The compounds of formula (I) can be used to form unsubstituted propargylic alcohols as set forth in Scheme B.

Scheme B

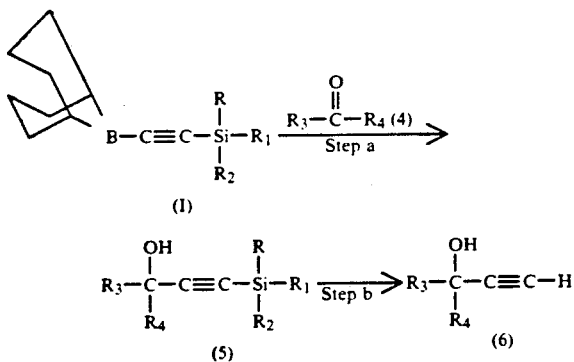

Scheme B provides a general method for using the compounds of formula (I) in order to form unsubstituted propargylic alcohols.

In step a, the appropriate B-(2-(trisubstituted-silyl)ethynyl)-9-borabicyclo[3.3.1]nonane of formula (I) is reacted with an appropriate aldehyde or ketone of structure (4) to give the corresponding 1-trisubstituted-silyl-1-alkyn-3-ol of structure (5).

For example, the appropriate B-(2-(trisubstituted-silyl)ethynyl)-9-borabicyclo[3.3.1]nonane of formula (I) is first contacted with an equimolar amount of an appropriate aldehyde or ketone of structure (4). The reactants are typically contacted in a suitable inert organic solvent such as pentane, hexane, tetrahydrofuran, methylene chloride and the like with pentane being preferred. The reactants are typically stirred together for a period of time ranging from 30 minutes to 10 days and at a temperature range of from 0° C. to reflux. For example, if pentane is the preferred solvent, reflux temperature would be 36° C. The intermediate borinate ester thus formed is recovered from the reaction zone by evaporation of the solvent.

The intermediate borinate ester is contacted with an equimolar amount of a suitable base such as ethanolamine, N,N-dimethylethanolamine, 2-(methylamino)ethanol, 2- C (ethylamino)ethanol, 2-amino-1-butanol, 2-amino-2-methyl-1-propanol, 1-amino-2-propanol, 2-amino-1-propanol propanol and the like with ethanolamine being preferred and an equimolar amount of a suitable alcohol such as methanol, ethanol, propanol and the like with methanol being preferred. The reactants are typically contacted in a suitable inert organic solvent such as ethyl ether, tetrahydrofuran, hexane, pentane, methylene chloride and the like with ethyl ether being preferred. The reactants are typically stirred together for a period of time ranging from 2-24 hours at a temperature range of from 0° C to reflux. The 1-trisubstitutedsilyl-1-alkyn-3-ol of structure (5) is recovered from the reaction zone by separation from the solid borate salts followed by extractive methods as is known in the art. It may be purified by silica gel chromatography.

It is preferred that the B-(2-(trisubstituted-silyl)ethynyl) -9-borabicyclo[3.3.1]nonane of formula (I) is one wherein R, R$_1$ and R$_2$ are each methyl.

An appropriate aldehyde or ketone of structure (4) is one wherein R$_3$ is hydrogen, a phenyl group substituted with any of the groups represented by C$_1$-C$_6$ alkoxy, phenyl or halogen or a C$_1$-C$_{12}$ alkyl of straight or branched chain configuration, unsubstituted or substituted with any of the groups represented by C$_1$-C$_6$ alkoxy, phenyl or halogen and R$_4$ refers to a phenyl group substituted with any of the groups represented by C$_1$-C$_6$ alkoxy, phenyl or halogen or C$_1$-C$_{12}$ alkyl of straight or branched chain configuration, unsubstituted or substituted with any of the groups represented by C$_1$-C$_6$ alkoxy, phenyl or halogen. The groups R$_3$ and R$_4$ together can be represented by a C$_5$-C$_7$ cycloalkyl.

In step b, the trisubstitutedsilyl group of the appropriate 1-trisubstituted-silyl-1-alkyn-3-ol of structure (5) is removed by techniques and procedures well known and appreciated by one of ordinary skill in the art to give the corresponding propargylic alcohol of structure (6).

For example, the appropriate 1-trisubstitutedsilyl-1-alkyn-3-ol of structure (5) is contacted with a slight molar excess of a suitable fluoride source, such as tetra-n-butylammonium fluoride, potassium fluoride, cesium fluoride and the like with tetra-n-butylammonium fluoride being preferred. The reactants are typically contacted in a suitable inert organic solvent such as tetrahydrofuran, diethyl ether, hexane, methylene chloride and the like, tetrahydrofuran being preferred. The reactants are typically stirred together for a period of time ranging from 15 minutes to 16 hours at a temperature range of from 0° C. to room temperature. The propargylic alcohol of structure (6) is recovered from the reaction zone by extractive methods as is known in the art. It may be purified by silica gel chromatography.

Alternatively, the trisubstitutedsilyl group of the appropriate 1-trisubstitutedsilyl-1-alkyn-3-ol of structure (5) may be removed by several other reagent combinations, including sodium hydroxide in aqueous methanol, ethanolic silver nitrate followed by sodium cyanide, and methyllithium-lithium bromide complex in ether as described in "Silicon in Organic Synthesis", E. W. Colvin, Robert E. Krieger (1981).

Starting materials for use in Scheme B are readily availiable to one of ordinary skill in the art.

The following examples present typical methods of using the compounds of formula (I) in order to form unsubstituted propargylic alcohols. These examples are understood to be illustrative only and are not intended to limit the scope of the present invention in any way.

EXAMPLE 2

1-Decyn-3-ol

Step a: 1-Trimethylsilyl-1-decyn-3-ol

Dissolve B-(2-(trimethylsilyl)ethynyl)-9-borabicyclo[3.3.1]nonane.tetrahydrofuran complex (2.4 g, 8.3 mmol) in pentane (25 mL) and add octylaldehyde (1.3 mL, 8.3 mmol). Stir at room temperature for 40 minutes and evaporate the solvent under a positive pressure of nitrogen to give a yellow solid. Add ethyl ether (30 mL) and methanol (336 μL, 8.3 mmol), cool to 0° C. and add, by dropwise addition, ethanolamine (0.5 mL, 8.3 mmol). Stir overnight, centrifuge the reaction mixture and separate the clear supernatant liquid. Wash the precipitate with pentane (2×10 mL) and combine the organic phases. Wash with water (2×25 mL) and dry (MgSO$_4$). Evaporate the solvent in vacuo and purify by silica gel chromatography (19:1 hexane/ethyl acetate) to give the title compound as a clear liquid (1.71 g, 91%).

$^1$H NMR (CDCl$_3$) δ0.164 (s, 9H), 1.13 (t, 3H), 2.23–1.35 (m, 13H), 4.25 (m, 1H); IR (neat) 3550–3150 (br), 2967, 2925, 2868, 2190, 1470, 1251 (s), 848 (vs) cm$^{-1}$.

Step b: 1-Decyn-3-ol

Dissolve 1-trimethylsilyl-1-decyn-3-ol (2.07 g, 9.13 mmol) in tetrahydrofuran (11 mL) and place under an argon atmosphere. Add, by dropwise addition, tetra-n-butylammonium fluoride (11 mL of a 1M solution in tetrahydrofuran, 11 mmol). Stir for 1 hour at room temperature and partition between methylene chloride and water. Separate the organic phase, wash with saturated aqueous sodium chloride, dry (MgSO$_4$), filter and evaporate the solvent in vacuo to give the title compound.

EXAMPLE 3

5-Phenyl-1-pentyl-3-ol

Step a: 5-Phenyl-1-trimethylsilyl-1-pentyl-3-ol

Dissolve B-(2-(trimethylsilyl)ethynyl)-9-borabicyclo[3.3.1]nonane.tetrahydrofuran complex (2.20 g, 7.6 mmol) in pentane (25 mL) and add hydrocinnamaldehyde (1.0 mL, 7.6 mmol). Stir at room temperature for 6 hours. Remove the solvent under a positive nitrogen pressure to give an orange solid. Add ethyl ether (30 mL) and methanol (310 μL, 7.6 mmol). Cool to 0° C. and add, by dropwise addition, ethanolamine (460 μL, 7.6 mmol). Stir overnight, centrifuge the reaction mixture and separate the clear supernatant liquid. Wash the precipitate with pentane (2×10 mL) and combine the organic phases. Wash with water (2×25 mL) and dry (MgSO$_4$). Evaporate the solvent in vacuo and purify by silica gel chromatography (19:1 hexane/ethyl acetate) to give the title compound as a pale yellow liquid (1.57 g, 89%).

$^{13}$C NMR (CDCl$_3$) 141.2, 128.4, 128.3, 125.4, 106.6, 89.6, 61.9, 39.1, 31.3, –0.181 ppm; $^1$H NMR (CDCl$_3$) δ0.161 (s, 9H), 2.00 (m, 2H), 2.42 (br, 1H), 2.78 (t, 2H), 4.34 (t, 1H), 7.26 (m, 5H); IR (neat) 3600–3250 (br), 3027, 2960, 2945, 2865, 2188, 1495, 1455, 1253 (s), 1048, 848 (vs), 760, 701 cm$^{-1}$.

Step b: 5-Phenyl-1-pentyl-3-ol

Dissolve 5-phenyl-1-trimethylsilyl-1-pentyl-3-ol (2.12g, 9.13 mmol) in tetrahydrofuran (11 mL) and place under an argon atmosphere. Add, by dropwise addition, tetra-n-butylammonium fluoride (11 mL of a 1M solution in tetrahydrofuran, 11 mmol). Stir for 1 hour at room temperature and partition between methylene chloride and water. Separate the organic phase, wash with saturated aqueous sodium chloride, dry (MgSO$_4$), filter and evaporate the solvent in vacuo to give the title compound.

EXAMPLE 4

4,4-Dimethyl-1-pentyn-3-ol

Step a: 4,4-Dimethyl-1-trimethylsilyl-1-pentyn-3-ol

Dissolve B-(2-(trimethylsilyl)ethynyl)-9-borabicyclo[3.3.1]nonane.tetrahydrofuran complex (2.13 g, 7.3 mmol) in pentane (25 mL) and add trimethylacetaldehyde (795 μL, 7.3 mmol). Stir at room temperature for 5 days. Remove the solvent under a positive nitrogen pressure to give a yellow solid. Add ethyl ether (30 mL) and methanol (500 μL). Cool to 0° C. and add, by dropwise addition, ethanolamine (440 μL, 7.3 mmol). Stir overnight, centrifuge the reaction mixture and separate the clear supernatant liquid. Wash the precipitate with pentane (2×10 mL) and combine the organic phases. Wash with water (2×25 mL) and dry (MgSO$_4$). Evaporate the solvent in vacuo and purify by silica gel chromatography (19:1 hexane/ethyl acetate) to give the title compound as a clear liquid (1.25 g, 93%).

$^{13}$C NMR (CDCl$_3$) 105.6, 90.1, 71.7, 35.7, 25.2, –0.139 ppm; $^1$H NMR (CDCl$_3$) δ0.102 (s, 9H), 0.919 (s, 9H), 1.67 (s, 1H), 3.92 (d, 1H); IR (neat) 3600–3180 (br), 2975 (s), 2963, 2901, 2875, 2187, 1481, 1460, 1365, 1253 (s), 1065, 1008 (s), 882, 858 (s), 845 (vs), 712 cm$^{-1}$.

Step b: 4,4-Dimethyl-1-pentyn-3-ol

Dissolve 4,4-dimethyl-1-trimethylsilyl-1-pentyn-3-ol (1.68 g, 9.13 mmol) in tetrahydrofuran (11 mL) and place under an argon atmosphere. Add, by dropwise addition, tetra-n-butylammonium fluoride (11 mL of a 1M solution in tetrahydrofuran, 11 mmol). Stir for 1 hour at room temperature and partition between methylene chloride and water. Separate the organic phase, wash with saturated aqueous sodium chloride, dry (MgSO$_4$), filter and evaporate the solvent in vacuo to give the title compound.

EXAMPLE 5

(3S,4R)-4-Methoxy-4-methyl-1-octyn-3-ol and (3R,4R)-4-Methoxy-4-methyl-1-octyn-3-ol

Step a: (3S,4R)-4-Methoxy-4-methyl-1-trimethylsilyl-1-octyn-3-ol and 3R,4R)-4-Methoxy-4-methyl-1-trimethylsilyl-1-octyn-3-ol Dissolve B-(2-(trimethylsilyl)ethynyl)-9-borabicyclo[3.3.1]nonane.tetrahydrofuran complex (2.13 g, 7.3 mmol) in pentane (25 mL) and add (2R)-2-methyl-2-methoxyhexanal (1.06 g, 7.3 mmol). Stir at room temperature for 72 hours. Remove the solvent under a positive nitrogen pressure to give a yellow solid. Add ethyl ether (30 mL) and methanol (500 μL). Cool to 0° C. and add, by dropwise addition, ethanolamine (440 μL, 7.3 mmol). Stir overnight, centrifuge the reaction mixture and separate the clear supernatant liquid. Wash the precipitate with pentane (2×10 mL) and combine the organic phases. Wash with water (2×25 mL) and dry (MgSO$_4$). Evaporate the solvent in vacuo and purify by silica gel chromatography (19:1 hexane/ethyl acetate) to give (3S,4R)-4-methoxy-4-methyl-1-trimethylsilyl-1-octyn-3-ol as a clear liquid (900mg, 51%).

$^{13}$C NMR (CDCl3) 104.3, 90.7, 78.6, 67.5, 49.7, 33.7, 25.5, 23.3, 19.0, 13.9, −0.307 ppm; $^{1}$H NMR (CDCl3) δ0.145 (s, 9H), 0.895 (t, 3H), 1.19 (s, 3H), 1.30 (m, 4H), 1.66 (m, 2H), 2.48 (d, J=5.0 Hz, 1H), 3.24 (s, 3H), 4.28 (d, J=4.9 Hz, 1H); IR (neat) 3600-3120 (br), 2958 (s), 2940, 2186, 1465, 1375, 1250 (s), 1069 (s), 845 (vs), 760 cm$^{-1}$. (3R,4R)-4-methoxy-4-methyl-1-trimethylsilyl-1-octyn-3-ol eluted as a clear liquid (80 mg, 10%).

$^{13}$C NMR (CDCl3) 103.6, 90.7, 79.5, 67.2, 49.7, 33.6, 24.9, 23.1, 17.6, 13.9, −0.298 ppm; $^{1}$H NMR (CDCl3) δ0.146 (s, 9H), 0.890 (t, 3H), 1.22 (s, 3H), 1.26 (m, 4H), 2.47 (br, 1H), 3.21 (s, 3H), 4.33 (s, 1H); IR (neat) 3600-3120 (br), 2960 (vs), 2941 (vs), 2871, 2186, 1465, 1375, 1251 (s), 1065, 1055, 845 (vs), 760 cm$^{-1}$.

Step b: (3S,4R)-4-Methoxy-4-methyl-1-octyn-3-ol

Dissolve (3S,4R)-4-methoxy-4-methyl-1-trimethylsilyl-1-octyn-3-ol (90 mg, 0.37 mmol) in tetrahydrofu place under an argon atmosphere. Add, by dropwise addition, tetra-n-butylammonium fluoride (3.7 mL of a 1M solution in tetrahydrofuran, 3.7 mmol). Stir for 1 hour at room temperature and partition between methylene chloride and water. Separate the organic phase, wash with saturated aqueous sodium chloride and dry (MgSO4). Evaporate the solvent in vacuo and purify by silica gel chromatography (19:1 hexane/ethyl acetate) to give the title compound as a clear thick oil (55 mg, 87%).

$^{13}$C NMR (CDCl3) δ82.60, 78.61, 74.10, 67.38, 49.89, 33.89, 25.58, 23.37, 18.77, 14.10; $^{1}$H NMR (CDCl3) δ0.917 (m, 3H), 1.24 (s, 3H), 1.29 (m, 4H), 1.70 (m, 2H), 2.40 (t, 1H), 2.46 (d, 1H), 3.27 (s, 3H), 4.32 (d, 1H); IR (neat) 3600-3300 (br), 3323, 2976 (s), 2965 (s), 2867, 1471, 1452, 1085 cm$^{-1}$.

Step b: (3R,4R)-4-Methoxy-4-methyl-1-octyn-3-ol

Dissolve (3R,4R)-4-methoxy-4-methyl-1-trimethylsilyl-1-octyn-3-ol (40mg, 0.17 mmol) in tetrah place under an argon atmosphere. Add, by dropwise addition, tetra-n-butylammonium fluoride (1.4 mL of a 1M solution in tetrahydrofuran, 1.4 mmol). Stir for 1 hour at room temperature and partition between methylene chloride and water. Separate the organic phase, wash with saturated aqueous sodium chloride and dry (MgSO4). Evaporate the solvent in vacuo to give the title compound as a thick clear oil (21 mg, 75%).

$^{13}$C NMR (CDCl3) δ 82.22, 79.24, 74.06, 66.91, 49.80, 33.60, 25.15, 23.23, 17.78, 14.01; $^{1}$H NMR (CDCl3) δ0.916 (m, 3H), 1.26 (s, 3H), 1.26 (m, 4H), 1.73 (m, 2H), 2.43 (d, 1H), 2.47 (br, 1H), 3.26 (s, 3H), 4.36 (d, 1H); IR (neat) 3620-3310 (br), 3312, 2972 (s), 2965 (s), 2858, 1470, 1450, 1075 cm$^{-1}$

EXAMPLE 6

1-(1-Ethynyl)cyclohexanol

Step a: 1-(2-Trimethylsilyl-1-ethynyl)cyclohexanol

Dissolve B-(2-(trimethylsilyl)ethynyl)-9-borabicyclo[3.3.1]nonane° tetrahydrofuran complex (2.63g, 9 mmol) in pentane (25 mL) and add cyclohexanone (907 μL, 9 mmol). Stir at room temperature for 16 hours. Remove the solvent under a positive nitrogen pressure to give a yellow solid. Add ethyl ether (30 mL) and methanol (365 μL, 9 mmol). Cool to 0° C. and add, by dropwise addition, ethanolamine (543 μL, 9 mmol). Stir overnight, centrifuge the reaction mixture and separate the clear supernatant liquid. Wash the precipitate with pentane (2×10 mL) and combine the organic phases. Wash with water (2×25 mL) and dry (MgSO4). Evaporate the solvent in vacuo and purify by silica gel chromatography (19:1 hexane/ethyl acetate) to give the title compound as a white crystalline material (1.56g, 88%); mp 72°-73° C.

$^{13}$C NMR (CDCl3) δ109.6, 88.4, 68.7, 39.9, 25.2, 23.3, −0.010 ppm; lH NMR (CDCl3) δ0.138 (s, 9H), 1.21 (m, 2H), 1.53 (m, 4H), 1.65 (m, 2H), 1.85 (m, 2H), 2.05 (s, 1H); IR (KBr) 3400-3250 (br), 2937 (s), 2902, 2861, 2166, 1450, 1348, 1285, 1251 (s), 1169, 1075 (s), 975 (s), 866 (vs), 840 (vs), 760, 699 cm$^{-1}$.

Step b: 1-(1-Ethynyl)cyclohexanol

Dissolve 1-(2-trimethylsilyl-1-ethynyl)cyclohexanol (1.79 g, 9.13 mmol) in tetrahydrofuran (11 mL) and place under an argon atmosphere. Add, by dropwise addition, tetra-n-butylammonium fluoride (11 mL of a 1M solution in tetrahydrofuran, 11 mmol). Stir for 1 hour at room temperature and partition between methylene chloride and water. Separate the organic phase, wash with saturated aqueous sodium chloride, dry (MgSO4), filter and evaporate the solvent in vacuo to give the title compound.

EXAMPLE 7

3-Methyl-1-nonyn-3-ol

Step a: 1-Trimethylsilyl-3-methyl-1-nonyn-3-ol

Dissolve B-(2-(trimethylsilyl)ethynyl)-9-borabicyclo[3.3.1]nonane° tetrahydrofuran complex (2.63 g, 9 mmol) in tetrahydrofuran (30 mL) and add 2-octanone (1.41 mL, 9 mmol). Stir at 65° C. for 48 hours. Cool to room temperature and remove the solvent under a positive nitrogen pressure to give a yellow solid. Add ethyl ether (30 mL) and methanol (365 μL, 9 mmol). Cool to 0° C. and add, by dropwise addition, ethanolamine (543 μL, 9 mmol). Stir overnight, centrifuge the reaction mixture and separate the clear supernatant liquid. Wash the precipitate with pentane (2×10 mL) and combine the organic phases. Wash with water (2×25 mL) and dry (MgSO4). Evaporate the solvent in vacuo and purify by silica gel chromatography (20:5:1/ hexane, chloroform, methanol) to give the title compound as a pale yellow liquid (1,45 g, 71%).

$^{13}$C NMR (CDCl3) 109.8, 87.2, 68.4, 43.5, 31.6, 29.7, 29.3, 24.5, 22.5, 14.0, −0.059 ppm; $^{1}$H NMR (CDCl3) δ0.129 (s, 9H), 0.862 (m, 3H), 1.29 (m, 6H), 1.43 (s, 3H), 1.45 (m, 2H), 1.60 (m, 2H), 2.02 (br, 1H); IR (neat) 3550-3220 (br), 2975 (s), 2941 (s), 2865, 2179, 1470, 1258 (s), 939, 865 (s), 845 (vs), 765 cm$^{-1}$ Step b: 3-Methyl-1-nonyn-3-ol Dissolve 1-trimethylsilyl-3-methyl-1-nonyn-3-ol (1.94g, 9.13 mmol) in tetrahydrofuran (11 mL) and place under an argon atmosphere. Add, by dropwise addition, tetra-n-butylammonium fluoride (11 mL of a 1M solution in tetrahydrofuran, 11 mmol). Stir for 1 hour at room temperature and partition between methylene chloride and water. Separate the organic phase, wash with saturated aqueous sodium chloride, dry (MgSO4), filter and evaporate the solvent in vacuo to give the title compound.

The following unsubstituted propargylic alcohols can be prepared by the method described in Examples 2-7:
5-Methyl-1-octyne-3-ol;
1-Octyne-3-ol;

3-Methyl-l-octyne-3-ol;

4.4-Dimethyl-l-octyne-3-ol;

Methyl[8-(4-methyl-l-octyn-3-ol)]ether;

2-Chlorophenyl[4-(l-butyne-3-ol)]ether;

2-Trifluoromethylphenyl[4-(l-butyne-3-ol)]ether;

Phenyl[4-(1-butyne-3-ol)]ether.

What is claimed is:

1. A compound of the formula

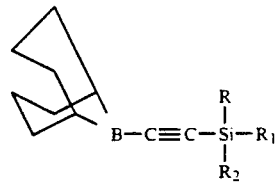

wherein R, $R_1$ and $R_2$ are each independently selected from a group represented by $C_1$–$C_6$ alkyl or phenyl.

2. A compound of claim 1 wherein R, $R_1$ and $R_2$ are each represented by methyl.

UNITED STATES PATENT AND TRADEMARK OFFICE
CERTIFICATE OF CORRECTION

PATENT NO.    : 5,110,966
DATED         : May 5, 1992
INVENTOR(S)   : Jonathon C. Evans and Christian T. Goralski It is certified that error appears in the above-identified patent and that said Letters Patent is hereby corrected as shown below:

Column 2, lines 55-56, the patent reads: "$-CH_2(CH_2-)_3$" and should read -- $-CH_2(CH_2)_3CH_3$, --.

Column 2, line 59, the patent reads: "$-CHhd2CH_3$" and should read -- $-CH_2CH_3$, --.

Column 4, line 51-52, the patent reads: "(25 mL of a 1M solution, stir at" and should read -- (25 mL of a 1M solution, 25mmol) and stir at --.

Column 6, lines 1-2, the patent reads: "2-amino-1-propanol propanol" and should read -- 2-amino-1-propanol, 3-amino-1-propanol --.

Column 9, line 3, the patent reads: "(CDC13)" and should read --$(CDCl_3)$ --.

Column 9, line 10, the patent reads: "(80 mg, 10%)" and should read -- (180 mg, 10%) --.

UNITED STATES PATENT AND TRADEMARK OFFICE
CERTIFICATE OF CORRECTION

PATENT NO. : 5,110,966
DATED : May 5, 1992
INVENTOR(S) : Jonathan C. Evans and Chrisitan T. Goralski It is certified that error appears in the above-identified patent and that said Letters Patent is hereby corrected as shown below:

Column 9, line 11, the patent reads: "(CDC13)" and should read --(CDCl$_3$) --.

Column 9, line 39, the patent reads: "tetrahydrofu place" and should read -- tetrahydrofuran (2mL) and place --.

Column 9, line 39, the patent reads: "tetrah place" and should read -- tetrahydrofuran (1mL) and place --.

Column 9, line 49, the patent reads: "(CDC13) 6 82.22," and should read -- (CDCl$_3$) δ 82.22, --.

Signed and Sealed this

Thirtieth Day of August, 1994

Attest:

*Attesting Officer*

BRUCE LEHMAN

*Commissioner of Patents and Trademarks*